(12) United States Patent
Herrera Ruiz et al.

(10) Patent No.: US 9,278,970 B2
(45) Date of Patent: Mar. 8, 2016

(54) CO-CRYSTALS OF TADALAFIL AND A HYDROXY-SUBSTITUTED BENZOIC ACID COFORMER AS PHOSPHODIESTERASE TYPE 5 INHIBITORS

(71) Applicant: Laboratorios Senosiain S.A. de C.V., Mexico City (MX)

(72) Inventors: Dea Herrera Ruiz, Cuernavaca (MX); Karina Mondragón Vásquez, Cuernavaca (MX); Hugo Morales Rojas, Cuernavaca (MX); Herbert Höpfl, Cuernavaca (MX); Juan Pablo Senosiain Peláez, Mexico City (MX)

(73) Assignee: Laboratorios Senosiain S.A. de C.V., Mexico City (MX)

( * ) Notice: Subject to any disclaimer, the term of this patent is extended or adjusted under 35 U.S.C. 154(b) by 0 days.

(21) Appl. No.: 14/412,272

(22) PCT Filed: Jul. 6, 2013

(86) PCT No.: PCT/IB2013/055530
§ 371 (c)(1),
(2) Date: Dec. 31, 2014

(87) PCT Pub. No.: WO2014/006604
PCT Pub. Date: Jan. 9, 2014

(65) Prior Publication Data
US 2015/0152107 A1    Jun. 4, 2015

(30) Foreign Application Priority Data

Jul. 6, 2012 (MX) .................. MX/a/2012/007915

(51) Int. Cl.
*C07D 241/38* (2006.01)
*C07D 471/14* (2006.01)
(52) U.S. Cl.
CPC .................................. *C07D 471/14* (2013.01)
(58) Field of Classification Search
CPC .................................................... C07D 241/38

USPC ........................................................ 544/343
See application file for complete search history.

(56) References Cited

FOREIGN PATENT DOCUMENTS

CA          2878360      *   1/2014
WO   WO 2010099323 A1      9/2010

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Chawla, et al. Current Research & Information on Pharmaceutical Sciences (CRIPS), 5(1), 2004, 9-12.*
D.R. Weyna et al., "Crystal Engineering of Multiple-Component Organic Solids: Pharmaceutical Cocrystals of Tadalfil with Persistent Hydrogen Bonding Motifs," Cryst Eng Comm, Apr. 2012, pp. 2377-2380, vol. 14.
International Search Report of Dec. 12, 2013, in English, for corresponding International Application No. PCT/IB2013/055530.

* cited by examiner

*Primary Examiner* — Douglas M Willis
(74) *Attorney, Agent, or Firm* — Stephen S. Hodgson

(57) ABSTRACT

The present invention relates to co-crystals of tadalafil with hydroxyl-substituted benzoic acid coformers having the following structure.

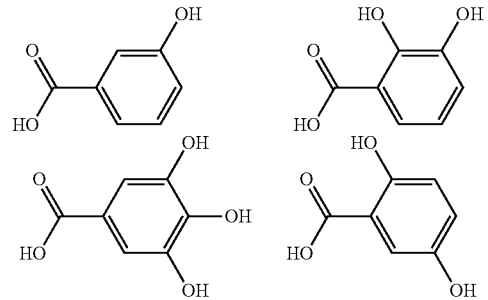

Said co-crystals can be used to produce a pharmaceutical composition containing the same as the useful active ingredient. Said co-crystals can exhibit a constant storage stability.

9 Claims, 10 Drawing Sheets

CO-CRYSTALS OF TADALAFIL AND A HYDROXY-SUBSTITUTED BENZOIC ACID COFORMER AS PHOSPHODIESTERASE TYPE 5 INHIBITORS

FIELD OF THE INVENTION

The present invention refers to new solid forms of phosphodiesterase type 5 inhibitors, in particular to complex cocrystals, and to the solvates, hydrates and polymorphs thereof, and their use in the manufacture of a pharmaceutical composition useful in the treatment of erectile dysfunction.

BACKGROUND OF THE INVENTION

The present invention relates to new solid forms (NSF) of phosphodiesterase type 5 inhibitors, particularly to complex crystals, which have a constant quality and which may have improved physicochemical properties such as the physical and chemical stability and a modified dissolution rate.

For the present invention, the new solid phases (NSP), are also called cocrystals and are obtained by means of technical experimentation. The cocrystals are chemical entities with physicochemical properties differing from those of the salts or polymorphs of the base active ingredient, including their salts and/or their polymorphs, due to the nature of the intermolecular interactions between the active molecule and a second solid constituent called coformer.

A cocrystal is a crystal formed by two or more non-identical molecules, in which the starting components are solid at room conditions when they are in their pure form, and wherein the two or more cocrystal components form aggregates that are characterized by being linked by intermolecular interactions—such as the Van der Waals forces, π-stacking, hydrogen bonding or electrostatic interactions—but without forming covalent bonds. By using crystal engineering techniques, a new compound with modified physicochemical properties differing from the polymorphs, salts, hydrates and/or the existing solvates, can be obtained. The adjustable screening parameters are higher, thus in the case of pharmaceutical ingredients, the physical and chemical properties of the active ingredient with clinical relevance may be optimized.

The pharmaceutical cocrystals are cocrystals containing at least one therapeutic molecule and a pharmaceutically acceptable coformer. In these crystals, their components—the active ingredient and the coformer—coexist in a well-defined stoichiometric ratio. The cocrystals in solid form tend to be more stable than the existing solvates or hydrates.

The present invention describes cocrystals which will be called "complex cocrystals", obtained from a phosphodiesterase type 5 inhibitor—tadalafil—and a neutral coformer, where both are solids at room temperature. The obtained cocrystals have a constant quality and may have improved physicochemical properties, such as a higher solubility and dissolution rate, enhanced flow properties and enhanced stability.

The phosphodiesterase type 5 inhibitors are a group of drugs used in the treatment of erectile dysfunction and for the treatment of pulmonary arterial hypertension. Structurally, they consist of heterocycles with nitrogen atoms, aromatic groups and carbonyl groups. The phosphodiesterease type 5 inhibitors used in the clinical practice are: tadalafil, sidenafil and vardenafil. In the present invention, a method for obtaining cocrystals and other solid forms based on one of these phosphodiesterase type 5 inhibitors, e.g., tadalafil, is developed.

The tadalafil molecule, as well as other phosphodiesterase type 5 inhibitors, is structurally comprised by heterocycles, aromatic groups and carbonyl groups. Tadalafil has an indole group, a pyrazine group and a benzodioxole attached to $C_6$ as shown in Scheme I.

Scheme I. Tadalafil structure

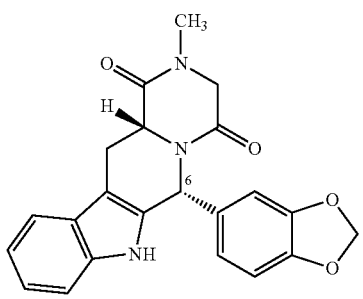

In the commercial pharmaceutical preparations, tadalafil is in neutral form and consists of the D+ isomer (6R,12R), which is almost insoluble in water. The absolute bioavailability of tadalafil after its oral delivery has not been yet determined. In therapeutic concentrations, 94% of the plasmatic tadalafil is bonded to proteins, it has a half life of 17.5 hours, and is eliminated by the hepatic metabolism, predominantly as metabolites, mainly in faeces (approximately 61% of the dose) and to a lesser extent in urine (approximately 36% of the dose). Tadalafil inhibits phosphodiesterase type 5 (PDE5) and enhances the erectile function by increasing the amount of the cyclic guanosine monophosphate (cGMP). The cGMP determines the relaxation of smooth muscle and increases the blood flow in the corpora cavernosa. Its delivery is by oral route in daily doses of 5, 10 or 20 mg.

Side effects of tadalafil are usually mild or moderate, transient, and improve without medical treatment. The most frequent side effects are: headache, dyspepsia, backache, myalgia, nasal stuffiness, flushing, dizziness and limb pain.

The drugs that inhibit CYP3A4 such as ketoconazole, ritonavir, erythromycin and itriconazole increase the exposure to tadalafil, as tadalafil is the CYP3A4 substrate, and are mainly metabolized by this route. On the other hand, the drugs that induce CYP3A4 such as rifampicine, carbamazepine, phenytoin and phenobarbital may decrease tadalafil exposure. Simultaneous delivery of an antacid such as aluminum hydroxide/magnesium hydroxide slows the tadalafil absorption rate. A substantial alcohol consumption (more than 5 units) in combination with tadalafil may increase the risk of orthostatic signs and symptoms, including increased heart rate, decreased blood pressure on standing, dizziness and headaches. When tadalafil is administered jointly with alpha-blocking agents such as tamsulosine, doxazosine or other anti-hypertensive agents such as amlodipine, metoprolol, bendrofluazide, enalapril or angiotensin II blockers, they may mutually enhance, in greater or lesser extent, its hypotensive effect.

Document US20090131667A1, describes the obtention and the process for manufacturing an amorphous form of tadalafil by assisted evaporation, with distillation of a tadalafil solution in an organic solvent. It also describes the obtention and the process for manufacturing the pure crystalline form B of tadalafil by precipitation of a tadalafil solution in a ketone solvent; and describes the preparation of a mixture of tadalafil form A and form B by precipitation of a tadalafil solution in an ester solvent.

Document US2006/0111571A1 (MX/a/2007/003719), describes the obtention and the process for making crystalline forms (polymorphs) I, II, III, IV, V, VI, VII and VIII of tadalafil by crystallization and/or precipitation in organic solvents; it describes the method of preparing the crystalline tadalafil form I by crystallizing tadalafil solutions in organic solvents such as 2-methoxyethanol, ethanol, acetonitrile, 1-propanol, isopropanol, ethyl acetate, toluene, dimethyl sulfoxide, n-butanol, methanol, chloroform, tetrahydrofuran, acetone and/or methyl ethyl ketone, and by precipitation when combining these solutions with solvents such as petroleum ether, cyclohexane, toluene, xylene, benzene and methyl-tert-butyl-ether, until obtaining a precipitate which was isolated. It describes the method for obtaining the crystalline form I starting from crystalline forms II, III and IV under certain humidity and temperature conditions; it describes the method for obtaining the crystalline form II from the crystallization of a tadalafil solution in acetone or methyl ethyl ketone or by precipitation adding a solvent such as petroleum ether, cyclohexane or methyl tert-butyl ether, to the methylethyl ketone solution; it describes the method for obtaining the crystalline form III of tadalafil, starting from the crystalline form II by heating at 65° C.; it describes the method for preparing the crystalline form IV, by crystallizing a tadalafil solution in methylene chloride or by precipitation from this solution with the addition of petroleum ether; it describes the method for obtaining of the crystalline form V from an acetic acid solution; it describes the obtention of the crystalline form VI using form IV by slurry in methanol and drying at 65° C.; it describes the obtention of tadalafil form VII using forms II, IV and V by slurry in toluene and drying at 65° C.; it describes the method for preparing the crystalline form VIII from the crystalline form IV in a range of 50-70° C.

The present invention, unlike the crystals cited in documents US20090131667A1 and US20060111571A1, comprises "complex" cocrystals which are obtained from a phosphodiesterase type 5 inhibitor such as tadalafil, using its polymorph I. The cocrystals of the present invention are obtained with coformers such as 3-hydroxybenzoic acid, 4-hydroxybenzoic acid, 2,3-dihydroxybenzoic acid, 2,5-dihydroxybenzoic acid, 3,4,5-trihydroxybenzoic acid, D-malic acid and L-tartaric acid. These coformers have one or more hydroxyl and carboxyl groups, forming an aggregate by hydrogen bonding and van der Waals interactions with tadalafil or other active ingredients that have structural similarities, such as sildenafil and vardenafil.

The application WO20120099323 describes the formation of tadalafil cocrystals with oxalic acid, salicylic acid, 4-hydroxybenzoic acid, malonic acid, 3-phenylpropanoic acid, methylparaben and propylparaben. Document Weyna et al., "Crystal engineering of multiple-component organic solids: Pharmaceutical cocrystals of tadalafil with persistent hydrogen bonding motifs", CrystEngComm, 2012. 14, 2377 describes the synthesis of tadalafil cocrystals with methylparaben, propylparaben, cinnamic acid and 4-hydroxybenzoic acid.

Although it is true that documents WO20120099323 and the Weyna et al. article describe the existence of tadalafil cocrystals, and even when during the process of obtaining cocrystals one may envisage a great amount of combinations with the possible coformers, not all the combinations produce a cocrystal or a stable solid form, as shown in the specification of the present application.

The present invention comprises new solid phases of tadalafil which may show enhanced physicochemical properties, such as a enhanced solubility, dissolution rate, bioavailability, stability and/or flow properties.

SUMMARY OF THE INVENTION

The present invention in the preferred embodiment provides several unpublished tadalafil compounds identified as complex cocrystals, formed by tadalafil form I and a neutral coformer. These new solid forms may have improved physicochemical and biopharmaceutical properties, which render them advantageous for the preparation of pharmaceutical compositions, such as enhanced bioavailability, enhanced solubility and hence fewer side effects.

In the preferred embodiment, the present invention comprises a process for preparing new solid forms of tadalafil, which may have enhanced features such as higher solubility, dissolution rate, better drug processing properties and/or better pharmacokinetic properties, which would allow for dose reduction and consequently for the reduction of side effects.

The present invention is specific for the obtention of NSF of phosphodiesterease type 5 inhibitors, such as tadalafil, by the solid phase transformation method (slurry), by the crystallization reaction method, and the chemical mechanical grinding method, with the use of minimum solvents and under environmental conditions that do not take it to the freezing point. This process of obtention lowers operation cost of the equipments for producing cocrystals, and has a minimal environmental impact as practically no organic solvents, or small quantities thereof, are used.

RATIONALE OF THE INVENTION

The rational use of drugs aims to obtain the greatest possible benefit for the people using them and to minimize economic costs, so it is important to have drugs which generate the same therapeutic effect with lower doses and consequently to reduce side effects, achieving a greater adherence to the treatment.

Sildenafil, vardenafil and tadalafil, which are selective cGMP inhibitors, specifically of phosphodiesterase type 5 (PDE5), have serious solubility problems in aqueous media, so there is a need for complex cocrystals which increase solubility and consequently their activity, and which allow for the reduction of the patient dose.

There are some prior art documents which disclose the obtention of tadalafil cocrystals, but the cocrystals and solvates disclosed herein are not described in the prior art. During the cocrystals obtention process, one could envisage a great amount of combinations with the possible coformers. However, not every combination produces a cocrystal or a stable solid form.

Although there is good understanding of the physicochemistry of the cocrystal components, their elucidation a priori is almost impossible, as the interactions which determine the structure are relatively weak and the number of degrees of freedom for the optimization problem is immeasurable. For these reasons, the new solid forms disclosed herein are not obvious to a person skilled in the art. Further, the cocrystals and solvates of the present invention have shown physicochemical stability, allowing their use in pharmaceutical compositions.

BRIEF DESCRIPTION OF THE DRAWINGS

FIG. 1. X-ray powder diffraction pattern of tadalafil cocrystal with 3-hydroxybenzoic acid.

FIG. 2. FT-infrared spectrum of the tadalafil cocrystal with 3-hydroxybenzoic acid.

FIG. 3. X-ray powder diffraction pattern of tadalafil cocrystal with 2,3-dihydroxybenzoic acid.

FIG. 4. FT-infrared spectrum of the tadalafil cocrystal with 2,3-dihydroxybenzoic acid.

FIG. 5. Crystalline structure of the tadalafil cocrystal with 3-dihydroxybenzoic acid.

FIG. 6. X-ray powder diffraction pattern of the tadalafil cocrystal with 2,5-dihydroxybenzoic acid.

FIG. 7. FT-infrared spectrum of the tadalafil cocrystal with 2,5-dihydroxybenzoic acid.

FIG. 8. X-ray powder diffraction pattern of the tadalafil cocrystal with 3,4,5-trihydroxybenzoic acid.

FIG. 9. FT-infrared spectrum of the tadalafil cocrystal with 3,4,5-trihydroxybenzoic acid.

FIG. 10. X-ray powder diffraction pattern of the tadalafil cocrystal with D-malic acid.

FIG. 11. FT-infrared spectrum of the tadalafil cocrystal with D-malic acid.

FIG. 12. Crystalline structure of the tadalafil cocrystal with D-malic acid.

FIG. 13. X-ray powder diffraction pattern of the tadalafil cocrystal with L-tartaric acid.

FIG. 14. FT-infrared spectrum of the tadalafil cocrystal with L-tartaric acid.

FIG. 15. X-ray powder diffraction pattern of the NSF formed with tadalafil and 4-hydroxybenzoic acid.

FIG. 16. DSC-TGA calorimetric analysis of the NSF formed with tadalafil and 4-hydroxybenzoic acid.

FIG. 17. FT-infrared spectrum of the NSF formed with tadalafil and 4-hydroxybenzoic acid.

FIG. 18. $^1$H NMR spectrum of the NSF formed with tadalafil and 3,4,5-trihydroxybenzoic acid.

FIG. 19. $^1$H NMR spectrum of the NSF formed with tadalafil and L-tartaric acid.

FIG. 20. $^1$H NMR spectrum of the NSF formed with tadalafil and 4-hydroxybenzoic acid.

DESCRIPTION OF THE INVENTION

Figure 1:
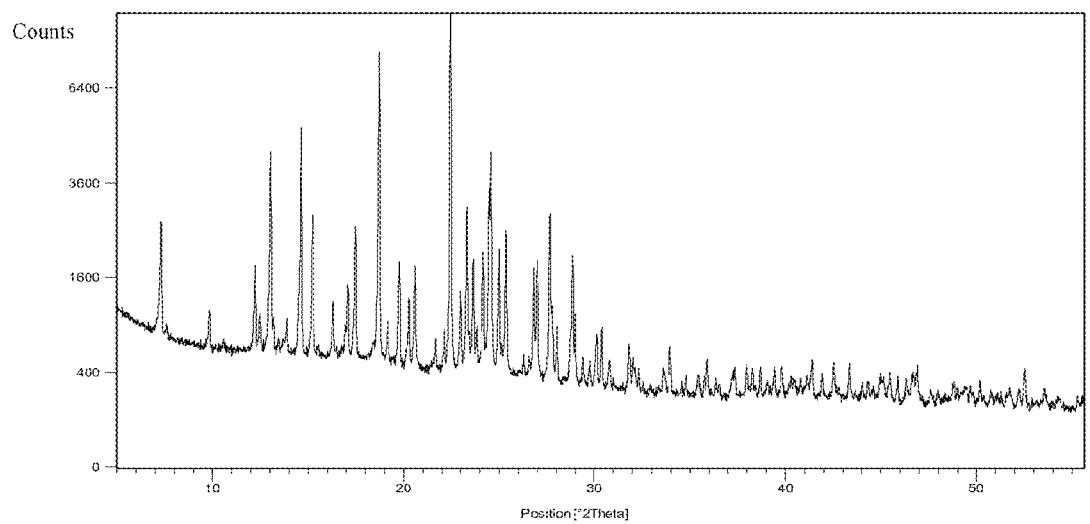
FIGS. 1-20 illustrate the results of the characterization of the tadalafil NSF obtained in the present invention.

One of the challenges faced during the development of the present invention consists in obtaining a stable compound formed with a phosphodiesterase type 5 inhibitor such as tadalafil, with high purity, with physicochemical properties suitable for preparing a pharmaceutical terms of stability, solubility and/or dissolution rate. Due to the complexity of the interactions in a solid structure, the final structure and thus the properties of the new solid forms are impossible to predict theoretically, therefore a large number of experiments had to be carried out in order to find the compounds described herein.

The complex cocrystals of the present invention, in the preferred embodiment, are formed with tadalafil form I and a neutral coformer, both being solids at room temperature. The NSF obtained from the combination of these solids is comprised by an aggregate in which the drug component and the neutral coformer molecule interact through hydrogen bonding and Van der Waals interactions. The new solid forms herein obtained offer the possibility of generating solids of active ingredients with improved physicochemical properties, such as enhanced solubility, stability or flowability.

The present invention started with a selective phosphodiesterase type 5 inhibitor, e.g., tadalafil.

Tadalafil was reacted with several possible coformers testing different solvents such as tetrahydrofuran (THF), methanol (MeOH), acetone or acetonitrile.

The synthesis strategies used for the obtention of the NSF of tadalafil were the crystallization reaction, the slurry method and the chemical mechanical grinding method.

The present invention worked, among others, with the following coformers: aliphatic carboxylic acids, aromatic carboxylic acids, aromatic hydroxycarboxylic acids, aliphatic hydroxycarboxylic acids, aromatic heterocyclic amides, amino acid derivatives, polyphenols, alcohols such as xylitol and aromatic aminocarboxylic acids such as 3-aminobenzoic acid. A new solid form (NSF) which was stable with 3-hydroxybenzoic acid was found in the different assays of the present invention. The obtained NSF corresponds to a compound wherein the neutral coformer has a hydroxyl group and a carboxylic acid, and further contains a phenyl group as part of its structure.

In addition, and in order to delimit the structural diversity of the coformers that generate cocrystals, other reactions were carried out, now with aliphatic and aromatic carboxylic acids, such as oxalic, succinic, adipic, maleic, benzoic, phthalic and acetylsalicylic acids. No NSF were obtained as a result of working with aliphatic and aromatic dicarboxilic acids.

Furthermore, reactions with aromatic monocarboxylic acids with a hydroxyl group, such as 2-hydroxybenzoic acid, 3-hydroxybenzoic acid, 4-hydroxybenzoic acid, mandelic acid and 1-hydroxy-2-naphtoic acid were performed. In this case, NSF were obtained with 3-hydroxybenzoic acid and 4-hydroxybenzoic acid.

Other reactions were performed with aromatic monocarboxylic acids, with two and three hydroxyl groups corresponding to vanillic acid, 2,3-dihydroxybenzoic acid, 2,4-dihydroxybenzoic acid, 2,5-dihydroxybenzoic acid, 2,6-dihydroxybenzoic acid, 3,4-dihydroxybenzoic acid, 3,5-dihydroxybenzoic acid and 3,4,5-trihydroxybenzoic acid, also known as gallic acid. In this case, NSF were obtained with 2,3-hydroxybenzoic acid, 2,3-dihydroxybenzoic acid and 3,4,5-trihydroxybenzoic acid. However, no NSF were obtained with 3,4-dihydroxibenzoic acid and 3,5-dihydroxibenozic acid, which again shows that the formation of NSF is unpredictable.

Also, reactions with aliphatic hydroxycarboxylic coformers such as glycolic, D-tartaric, L-tartaric, D,L-tartaric, mesotartaric, D-Malic, L-Malic, DL-Malic and citric acids were performed. In this case, NSF were obtained with D-malic acid and L-tartaric acid.

In other cases, in order to obtain NSF and to determine whether the substitution of the alcohol group with an amine influenced the NSF obtention, the reaction of 3-aminobenzoic acid—in analogy to the 3-hydroxybenzoic acid—was assessed. In this case, no NSF was obtained.

Similarly, and in order to determine the NSF formation with molecules containing another type of hydrogen bonding donors, aside from carboxylic and hydroxy groups, amino acids such as L-glutamine, L-phenylalanine, L-serine, L-threonine and L-tyrosine were tested. As a result, no NSF were obtained with these coformers.

Reactions with benzamides such as picolinamide, nicotinamide and isonicotinamide and alcohols such as xylitol were also performed, which neither produced NSF.

Based on the results obtained for tadalafil, the formation of cocrystals with sildenafil and vardenafil is possible through the formation of intermolecular hydrogen bonding and Van der Waals interactions of the active ingredients with the neutral coformers, specifically those containing hydroxycarboxylic groups.

Results of the Obtention of NSF by Different Methods

In the preferred embodiment, equimolar mixtures of tadalafil and the corresponding coformers were prepared, to which a small amount of solvent was added to form a slurry, under constant stirring for 8 hours. With this method, several possible combinations between tadalafil, the coformers and the solvents were made. The product of these reactions was characterized by X-ray powder diffraction assay. This test showed the obtention of NSF either as cocrystals or as solvates thereof. From the results of these tests it is concluded that the cocrystals formation is not simple, nor predictable.

The slurry experiments with aliphatic and aromatic carboxylic acids, such as oxalic acid, succinic acid, adipic acid, maleic acid, benzoic acid, phthalic acid and acetylsalicylic acid in methanol or acetonitrile, evidenced through an X-ray powder diffraction analysis that in all cases the solid obtained with the saturated solution crystallization method corresponds exactly with tadalafil and/or the coformer, i.e., no NSF were obtained. Similar results were obtained with the amino acids, alcohols such as xylitol, amides and 3-aminocarboxylic acid.

Crystallization experiments carried out with aromatic hydroxycarboxylic acids rendered different results. For example, the NSF synthesis with 3-hydroxybenzoic acid and 4-hydroxybenzoic acid does proceed with the slurry crystallization, grinding or crystallization reaction methods using acetonitrile as solvent. The phase obtained with 3-hydroxybenzoic acid was also obtained from methanol. In contrast, none of the three methodologies allowed obtaining NSF with 2-hydroxybenzoic acid. These assays demonstrate that the crystallization reactions for the formation of cocrystals are not predictable.

Figure 2:
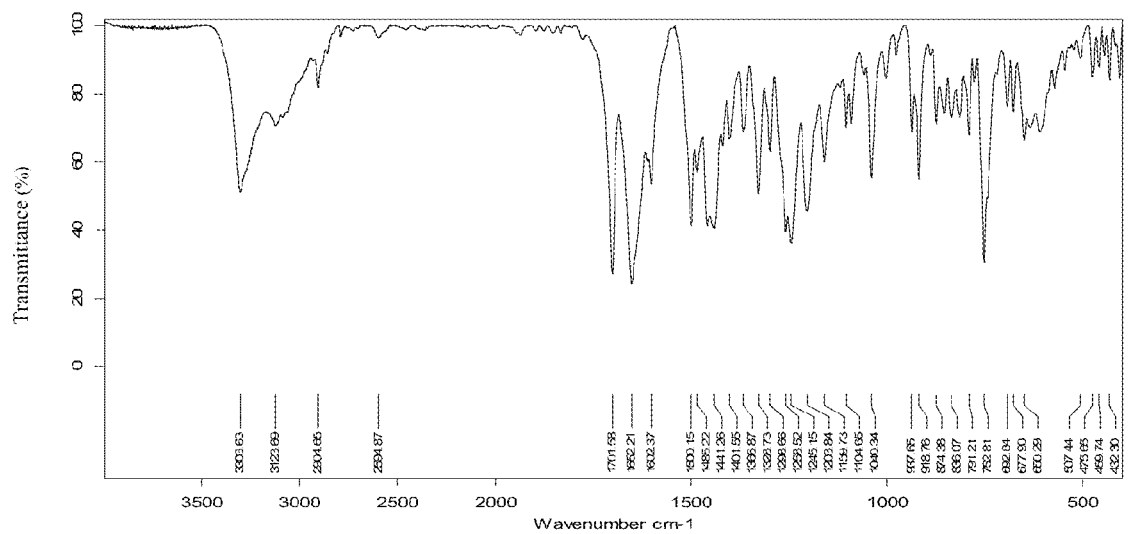
Figure 15:
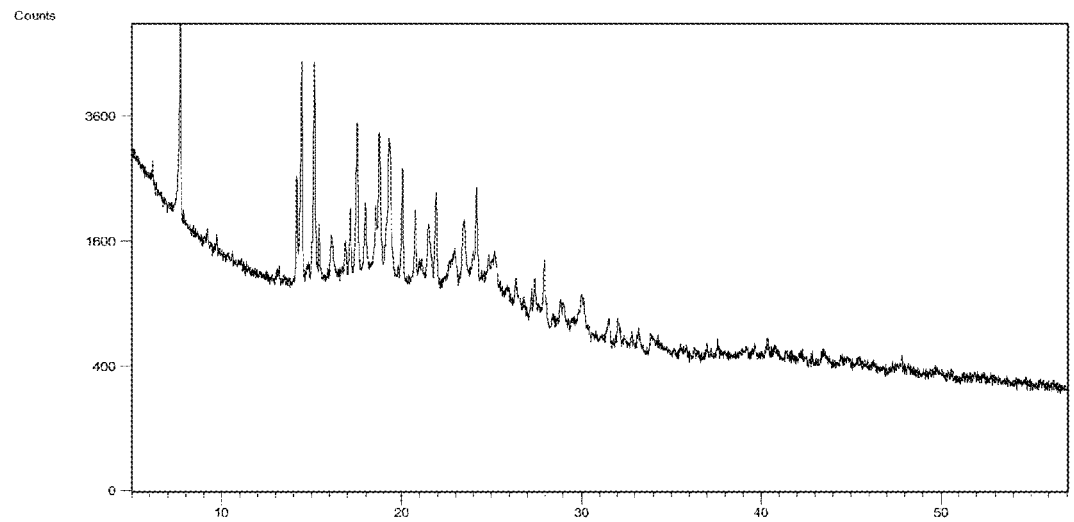
Figure 16:
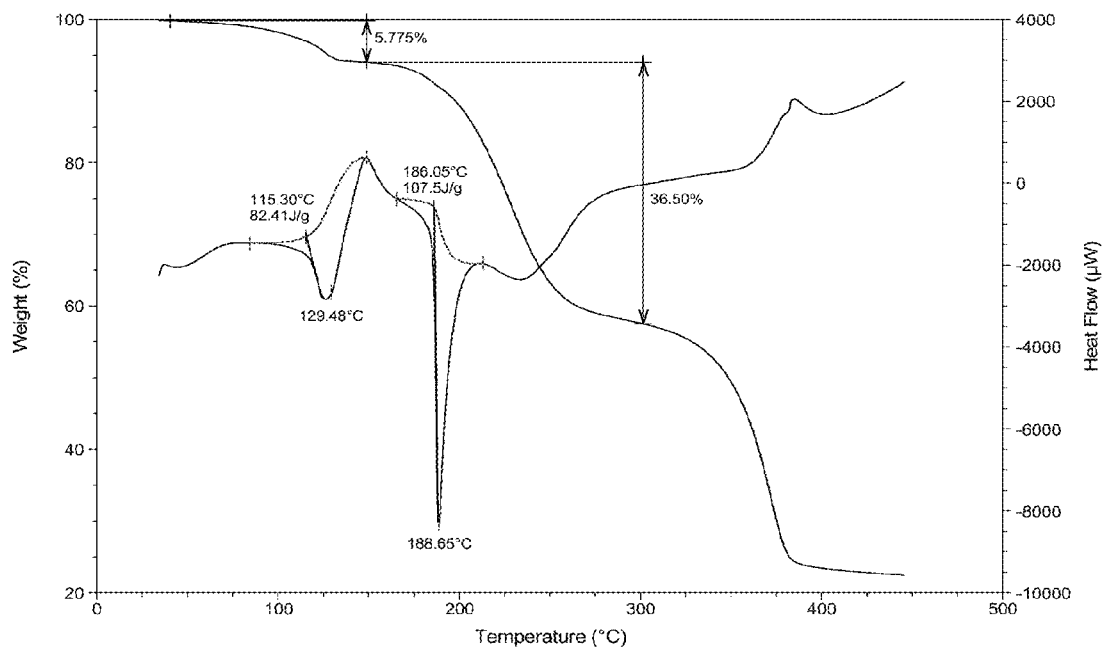
Figure 17:
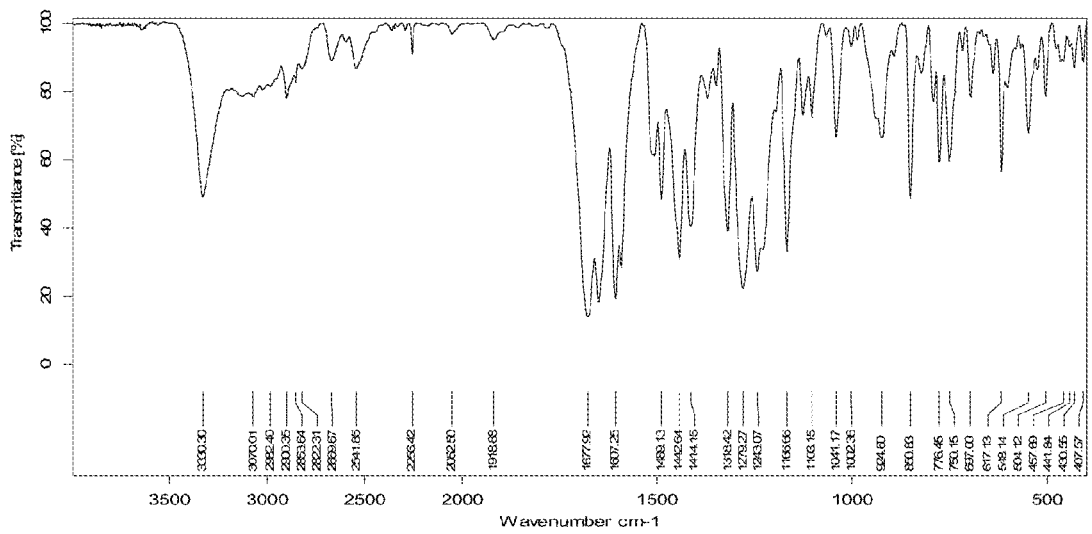
Figure 20:
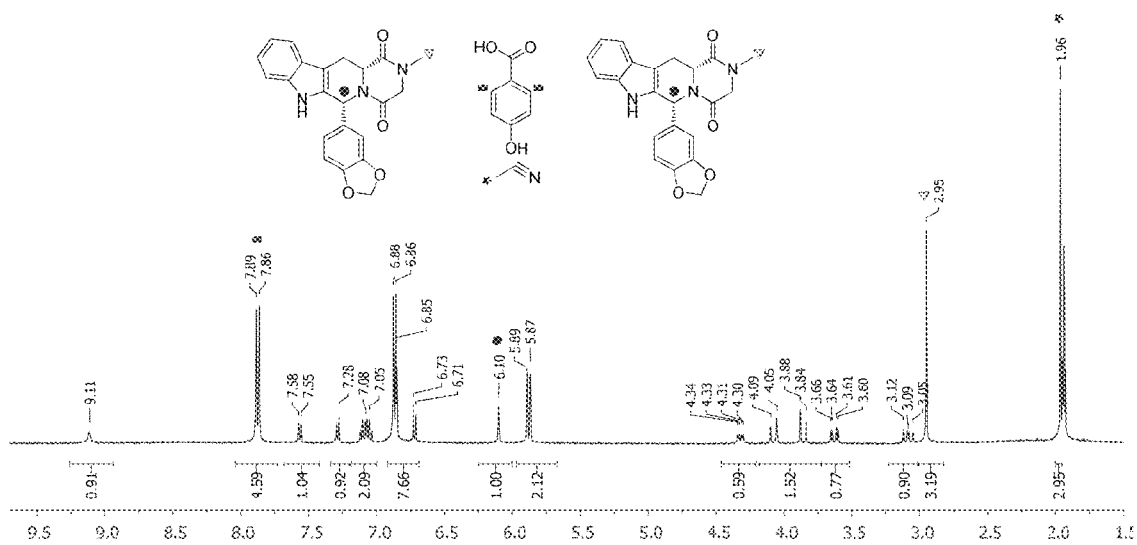

These new phases obtained were mainly verified with X-ray powder diffraction (XRD) analysis (FIGS. 1 and 15) and infrared spectrum (FT-IR) (FIGS. 2 and 17). Particularly, for the phase obtained with 4-hydroxybenzoic acid, the IR spectrum (FIG. 17) shows a band at 2250 cm$^{-1}$ which corresponds to the vibrational band of the cyano group, suggesting the formation of an acetonitrile solvate. To elucidate the stoichiometric ratio of the components of the obtained solvated cocrystal, a 1H Nuclear Magnetic Resonance analysis was performed (FIG. 20). This study shows that the solvated cocrystal with 4-hydroxybenzoic acid has a stoichiometry of 1:2:1 drug:coformer:solvent (acetonitrile). Finally, FIG. 16 shows the results of the differential scanning calorimetry analysis/thermogravimetric analysis (TGA/DSC) of the NSF formed with tadalafil and 4-hydroxybenzoic acid.

On the other hand, with dihydroxybenzoic acids using acetonitrile as the reaction medium, NSF were obtained with 2,3-hydroxybenzoic and 2,5-dihydroxybenzoic acids, but no new phases were obtained, for example, with 3,5-dihydroxybenzoic acid, 3,4-dihydroxybenzoic acid and 2,4-dihydroxybenzoic acid. Again, it is demonstrated that the the formation of cocrystals is unpredictable.

The NSF synthesis with 2,3-dihydroxybenzoic acid proceeds with the three aforementioned synthesis methodologies. However, the slurry and chemical mechanical reactions appear to be inefficient with 5-dihydroxybenzoic acid, but the NSF was indeed obtained with this coformer using the crystallization reaction method. The tadalafil NSF with 2,3-dihydroxybenzoic acid was also obtained using THF as reaction medium.

Figure 3:
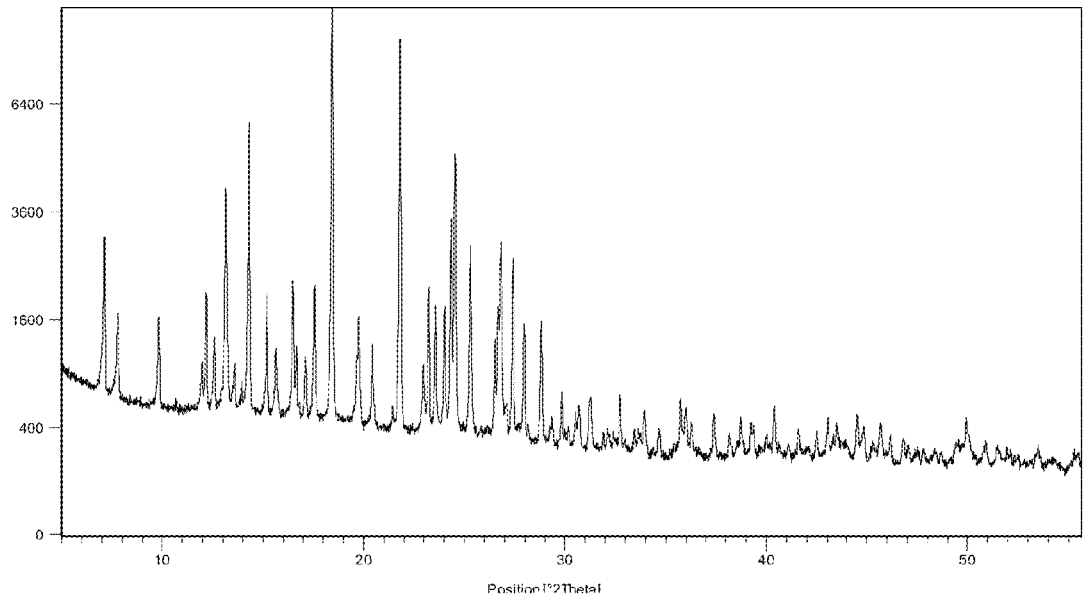
Figure 4:
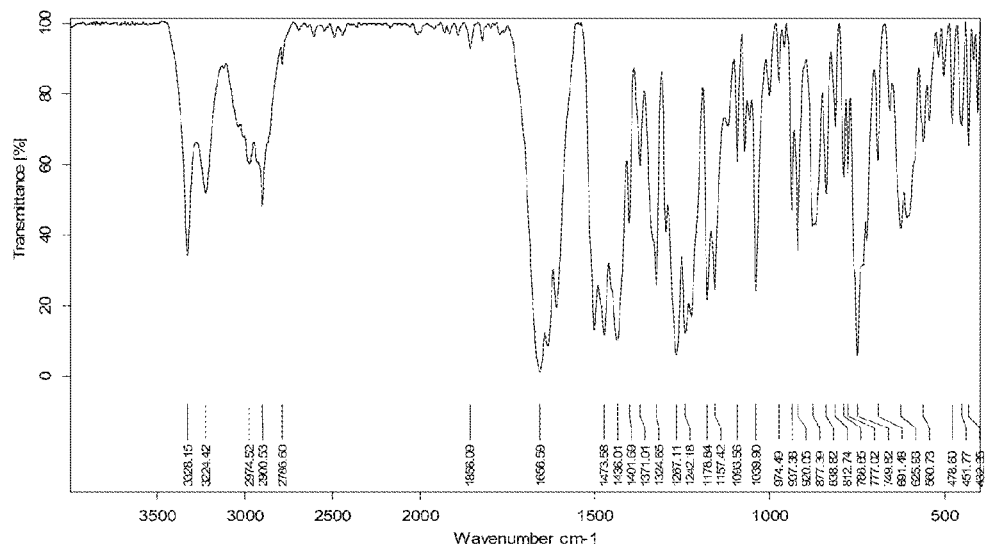
Figure 5:
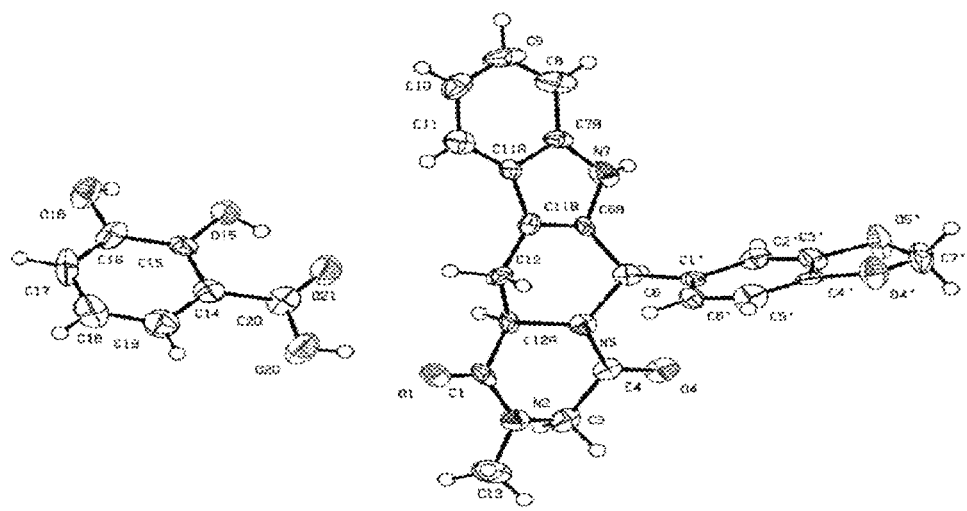
Figure 6:
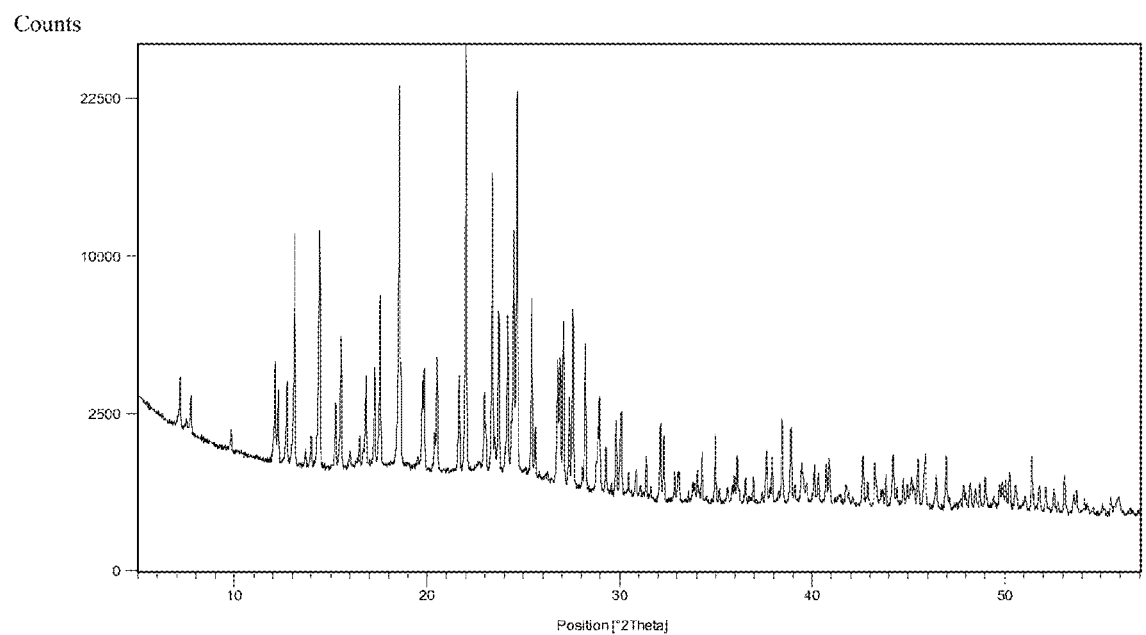
Figure 7:
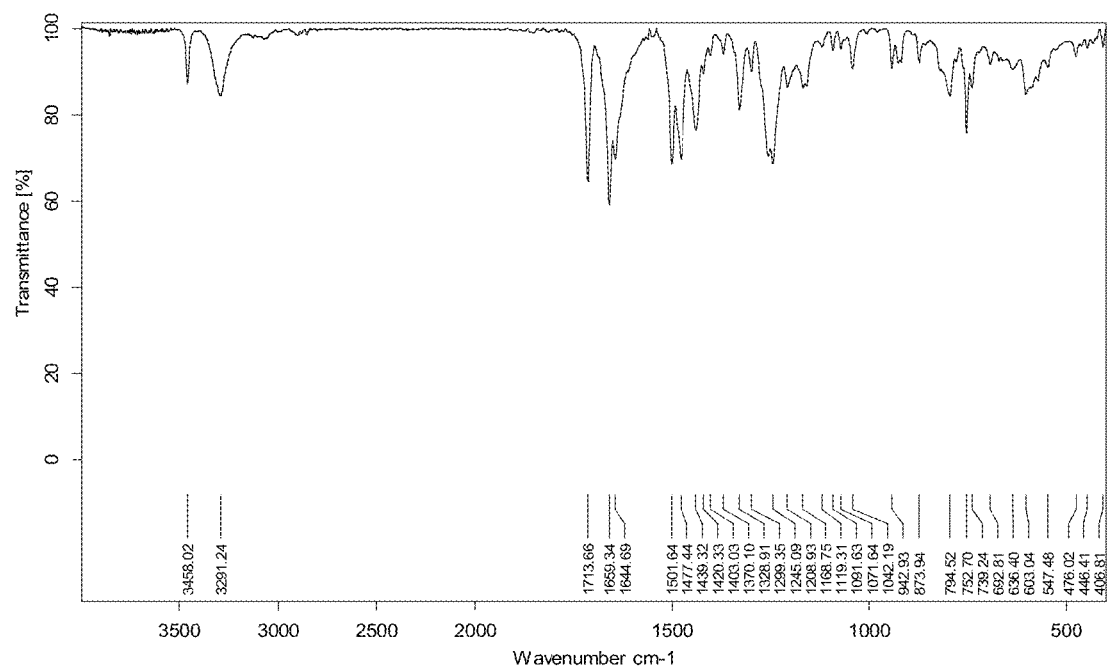

The NSF of tadalafil with 2,3-dihydroxybenzoic acid and 2,5-dihydroxybenzoic acid were analyzed using X-ray powder diffraction (XRD) and infrared spectrum (FT-IR). FIG. 3 shows X-ray powder diffraction pattern of the tadalafil cocrystal with 2,3-hydroxybenzoic acid. FIG. 4 shows the infrared spectrum (FT-IR). FIG. 5 shows the asymmetric unit of the crystalline structure of the tadalafil cocrystal with 2,3-hydroxybenzoic acid, as obtained with monocrystal X-ray diffraction. FIGS. 6 and 7 show the X-ray powder diffraction (XRD) pattern and the infrared spectrum FT-IR of the tadalafil cocrystal with 2,5-hydroxybenzoic acid.

Figure 8:
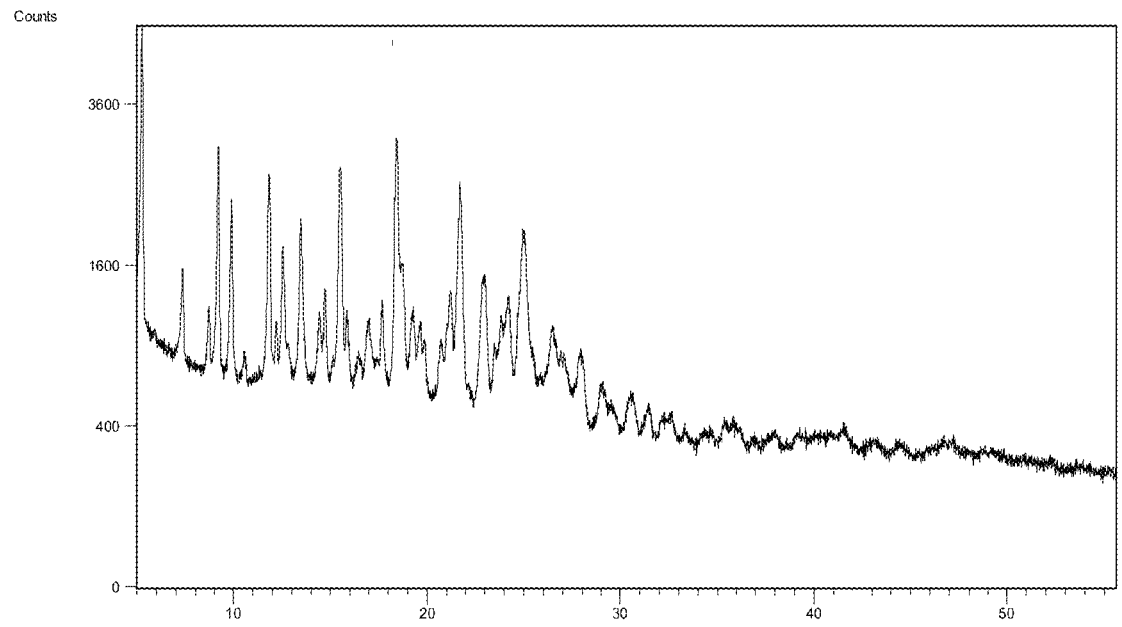
Figure 9:
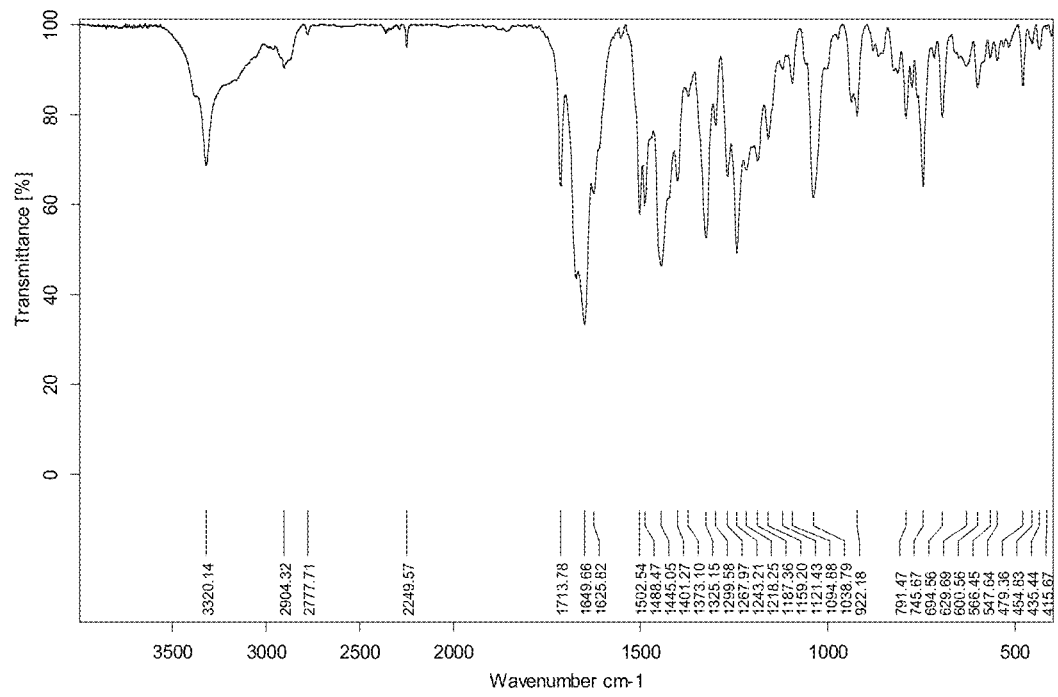
Figure 18:
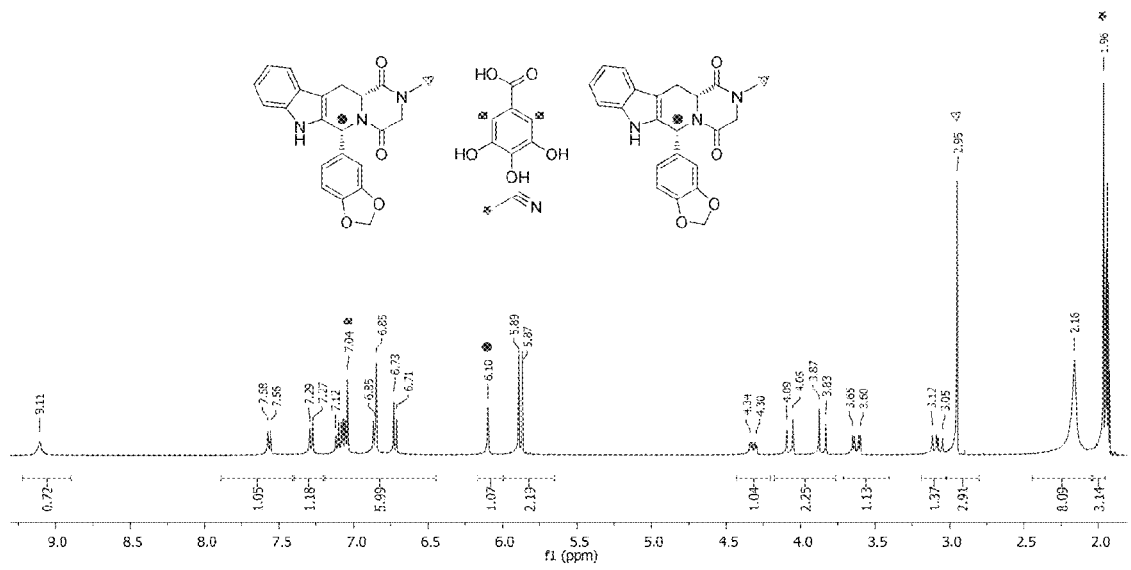

3,4,5-trihydroxybenzoic acid also produced a NSF (FIG. 8) in acetonitrile. The IR spectrum (FIG. 9) for this solid phase has a band at 2250 cm$^{-1}$, which corresponds to the vibrational band of the cyano group, suggesting the formation of an acetonitrile solvate. The 1H Nuclear Magnetic Resonance analysis (FIG. 18) shows that the solvated cocrystal with 3,4,5-trihydroxybenzoic acid has a stoichiometry of 2:1:1 drug:coformer:solvent (acetonitrile).

In the crystallization by slurry, grinding and/or saturated solutions of the coformer in acetonitrile using aliphatic hydroxycarboxylic acids, NSF with D-Malic acid and L-tartaric acid were obtained, but this was not the case with D-tartaric acid, DL-tartaric acid, meso-tartaric acid, L-Malic acid and DL-Malic acid. For the latter, the diffraction pattern of the obtained solid corresponds to that of tadalafil, demonstrating the formation of an enantiomerically selective molecular assembly.

Figure 10:
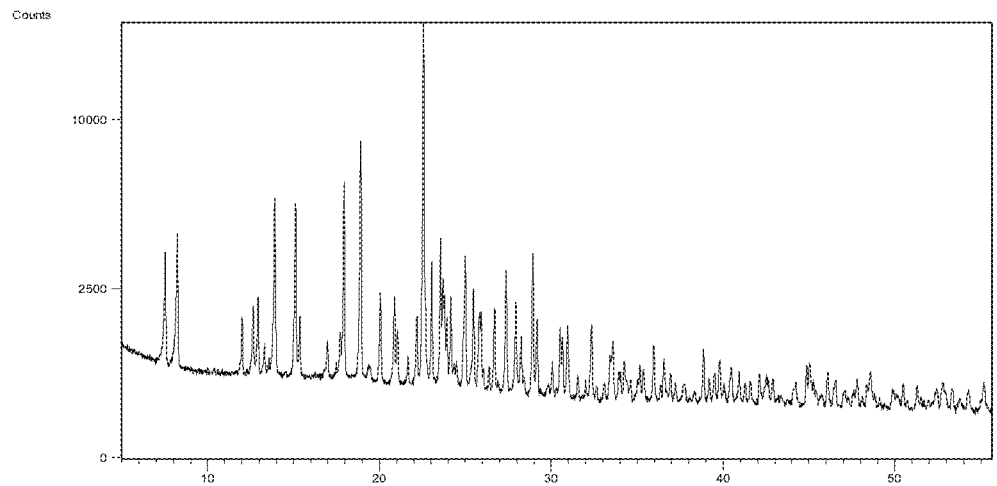
Figure 11:
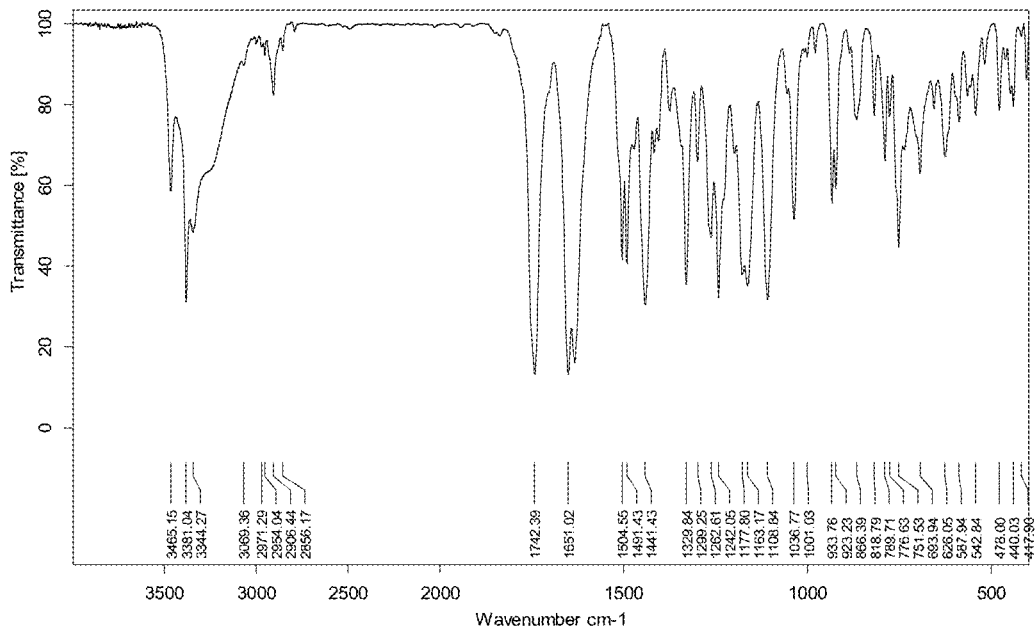
Figure 12:
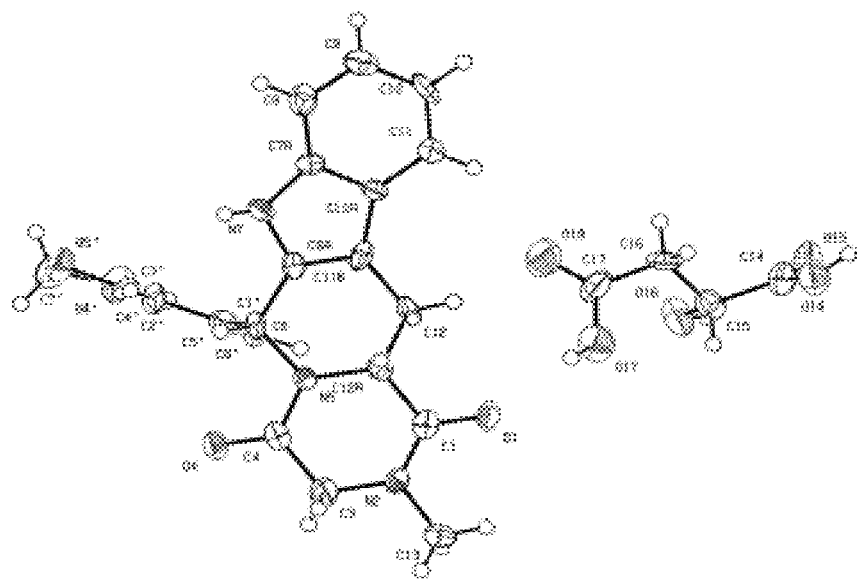
Figure 13:
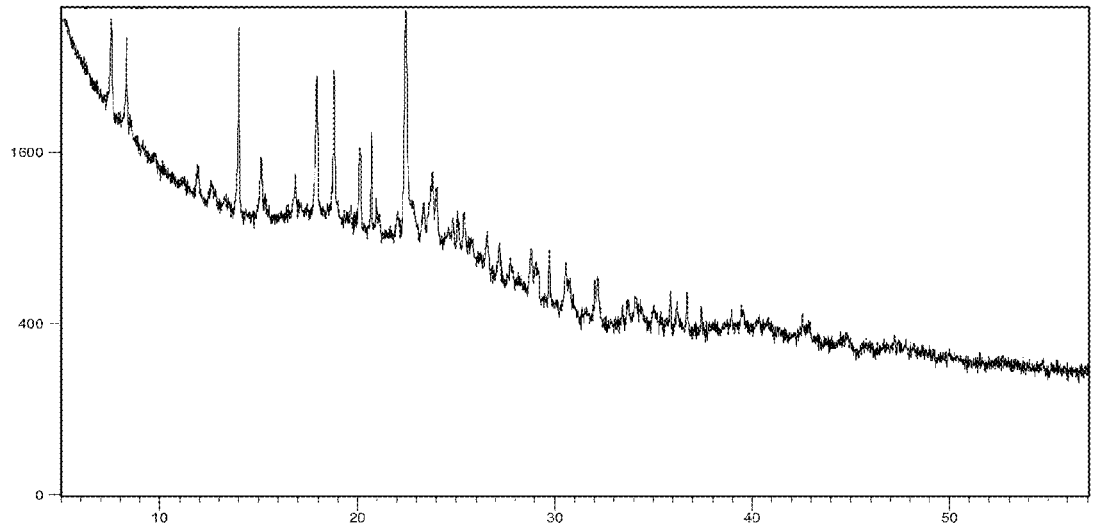
Figure 14:
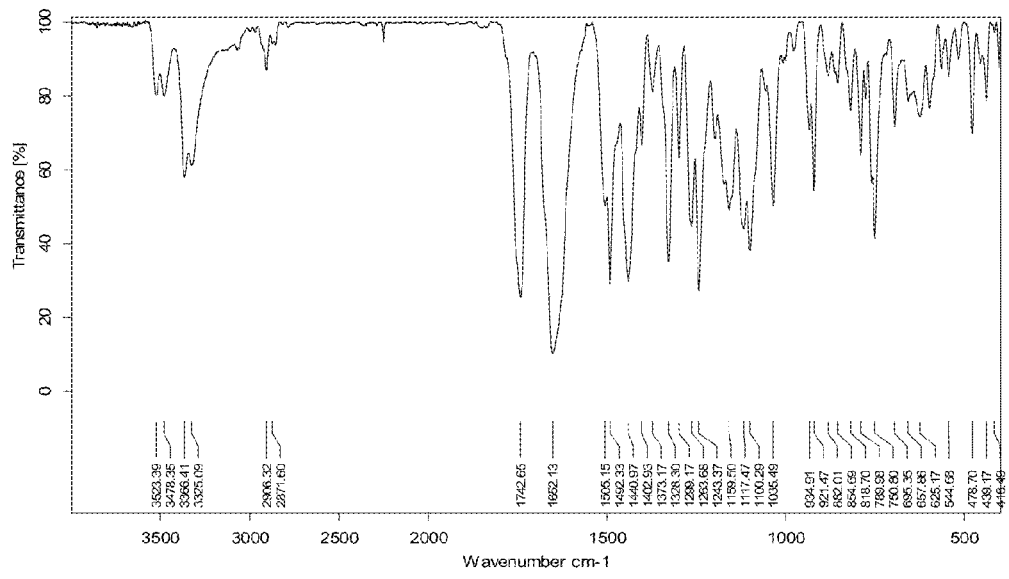

The obtention of tadalafil NFS with D-Malic acid and L-tartaric acid was verified with X-ray powder diffraction (XRD) (FIGS. 10 and 13) and infrared spectrum (FT-IR) (FIGS. 11 and 14). FIG. 12 shows the asymmetric unit of the crystalline structure of the tadalafil cocrystal with D-malic acid, obtained by monocrystal X-ray diffraction.

Figure 19:
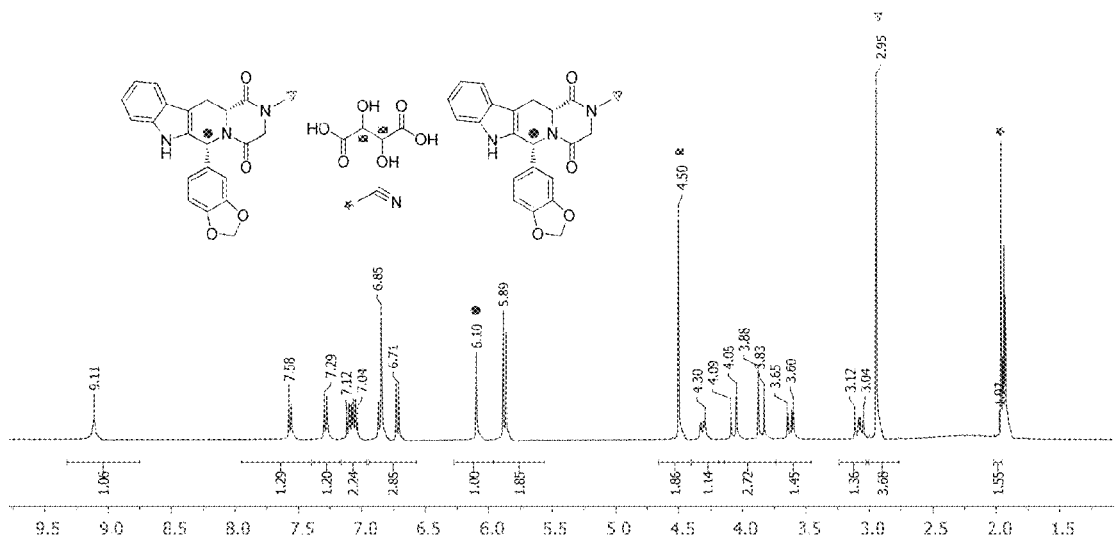

The IR spectrum for the NFS with tartaric acid (FIG. 14) has a band at 2250 cm$^{-1}$, which corresponds to the vibrational band of the cyano group, suggesting the formation of an acetonitrile solvate. To elucidate the stoichiometric ratio of the components of the solvated cocrystal, a 1H Nuclear Magnetic Resonance analysis was performed (FIG. 19). This study shows that the solvated cocrystal with L-tartaric acid has a stoichiometry of 2:1:1 drug:coformer:solvent (acetonitrile).

New Solid Phases (NSP) Obtained

In the preferred embodiment of the present invention, tadalafil NSF were obtained as a result of the experimentation. Some examples are listed below.

Combination of tadalafil with a chemical compound of the kind of aliphatic hydroxycarboxylic acids, such as D-malic acid and L-tartaric acid.

Combination of tadalafil with a chemical compound belonging to the aromatic hydroxycarboxylic acid derivatives, such as 3-hydroxybenzoic acid, 4-hydroxybenzoic acid, 2,3-dihydroxybenzoic acid, 2,5-dihydroxybenzoic acid and 3,4,5-dihydroxybenzoic acid.

What is claimed is:

1. A crystalline compound consisting of tadalafil of formula T and a coformer Y:

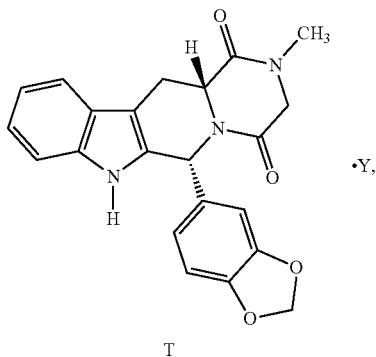

T or an acetonitrile solvate thereof,
wherein Y is selected from the group consisting of 3-hydroxybenzoic acid, 2,3-dihydroxybenzoic acid, 2,5-dihydroxybenzic acid and 3,4,5-trihydroxybenzoic acid.

2. The compound according to claim 1, wherein Y is 3,4,5-trihydroxybenzoic acid.

3. The compound according to claim 2, wherein the compound is an acetonitrile solvate.

4. The compound according to claim 3, wherein the T:Y:acetonitrile molar ratio is 2:1:1.

5. The compound according to claim 1, wherein Y is 3-hydroxybenzoic acid.

6. The compound according to claim 1, wherein Y is 2,3-dihydroxybenzoic acid.

7. The compound according to claim 1, wherein Y is 2,5-dihydroxybenzoic acid.

8. A method for inhibiting phosphodiesterase type 5 activity in a patient, comprising administering to said patient an effective amount of the compound according to claim 1.

9. A method for treating erectile dysfunction and/or pulmonary arterial hypertension in a patient, comprising administering to said patient an effective amount of the compound according to claim 1.

* * * * *